US008460723B2

(12) United States Patent
Søe et al.

(10) Patent No.: US 8,460,723 B2
(45) Date of Patent: *Jun. 11, 2013

(54) METHOD OF IMPROVING THE PROPERTIES OF A FLOUR DOUGH, A FLOUR DOUGH IMPROVING COMPOSITION AND IMPROVED FOOD PRODUCTS

(75) Inventors: Jørn Borch Søe, Mundelstrup (DK); Charlotte Horsmans Poulsen, Braband (DK); Pernille Bak Høstrup, Århus C (DK)

(73) Assignee: DuPont Nutrition Biosciences ApS, Copenhagen K (DK)

( * ) Notice: Subject to any disclaimer, the term of this patent is extended or adjusted under 35 U.S.C. 154(b) by 135 days.

This patent is subject to a terminal disclaimer.

(21) Appl. No.: 13/052,551

(22) Filed: Mar. 21, 2011

(65) Prior Publication Data
US 2012/0201928 A1 Aug. 9, 2012

Related U.S. Application Data

(60) Continuation of application No. 10/676,006, filed on Oct. 2, 2003, now Pat. No. 7,931,924, which is a division of application No. 09/932,923, filed on Aug. 21, 2001, now Pat. No. 6,726,942, which is a continuation of application No. 08/676,186, filed on Sep. 12, 1996, now Pat. No. 6,358,543, which is a continuation-in-part of application No. 08/483,870, filed as application No. PCT/DK96/00239 on Jun. 4, 1996, now abandoned.

(51) Int. Cl.
*A21D 2/00* (2006.01)

(52) U.S. Cl.
USPC .................. 426/18; 426/20; 426/64; 426/549; 426/653

(58) Field of Classification Search
USPC ............... 426/18, 19, 20, 22, 27, 61, 64, 549, 426/653
See application file for complete search history.

(56) References Cited

U.S. PATENT DOCUMENTS

| 2,783,150 | A | 2/1957 | Luther |
| 2,888,385 | A | 5/1959 | Felix |
| 3,368,903 | A | 2/1968 | Welch et al. |
| 3,520,702 | A | 7/1970 | Menzi |
| 4,160,848 | A | 7/1979 | Vidal et al. |
| 5,059,430 | A | 10/1991 | Bowles |
| 5,094,951 | A | 3/1992 | Rosenberg |
| 5,108,765 | A | 4/1992 | Maat et al. |
| 5,185,052 | A | 2/1993 | Chappell et al. |
| 5,232,846 | A | 8/1993 | Takeda et al. |
| 5,318,785 | A | 6/1994 | DeStefanis |
| 5,451,413 | A | 9/1995 | Fok et al. |
| 5,650,188 | A | 7/1997 | Gaubert et al. |
| 5,716,654 | A | 2/1998 | Groenendaal |
| 5,916,607 | A | 6/1999 | Mutsaers et al. |
| 6,039,983 | A | 3/2000 | Wagner et al. |
| 6,103,505 | A | 8/2000 | Clausen et al. |
| 6,110,508 | A | 8/2000 | Olesen et al. |
| 6,143,545 | A | 11/2000 | Clausen et al. |
| 6,251,626 | B1 | 6/2001 | Stougaard et al. |
| 6,254,903 | B1 | 7/2001 | Schuster et al. |
| 6,358,543 | B1 | 3/2002 | Soe et al. |
| 6,365,204 | B1 | 4/2002 | Spendler et al. |
| 6,406,723 | B1 | 6/2002 | Soe et al. |
| 6,726,942 | B2 | 4/2004 | Soe et al. |
| 6,852,346 | B2 | 2/2005 | Søe et al. |
| 6,924,366 | B2 | 8/2005 | Stougaard et al. |
| 6,936,289 | B2 | 8/2005 | Olsen et al. |
| 6,964,944 | B1 | 11/2005 | Callisen et al. |
| 6,967,035 | B2 | 11/2005 | Bojsen et al. |
| 7,226,771 | B2 | 6/2007 | Gramatikova et al. |
| 7,931,924 | B2 * | 4/2011 | Soe et al. ................ 426/20 |
| RE43,341 | E * | 5/2012 | Olsen et al. ............. 426/20 |
| 2001/0055635 | A1 | 12/2001 | Spendler et al. |
| 2002/0054577 | A1 | 5/2002 | Gaskill et al. |
| 2004/0235119 | A1 | 11/2004 | Hoppe et al. |
| 2005/0037391 | A1 | 2/2005 | Kragh et al. |
| 2006/0075518 | A1 | 4/2006 | Yaver et al. |

FOREIGN PATENT DOCUMENTS

| AR | 249546 | 5/1996 |
| AU | 199742798 | 4/1998 |
| CA | 805618 | 2/1969 |
| CA | 462382 | 6/1990 |
| CA | 2102723 | 9/1990 |
| CA | 2134597 | 4/1995 |
| CA | 2151978 | 12/1995 |
| CA | 2157718 | 3/1996 |
| CA | 2224143 | 12/1996 |
| CA | 2 403 025 | 4/2004 |
| CL | 858-1991 | 3/1992 |

(Continued)

OTHER PUBLICATIONS

Novozymes Annual Report 2002, "Success for new baking enzyme."
Hossen, Monjur, "Enzyme catalyzed synthesis of structured phospholipids with conjugated linoleic acid and plant sterols," A Dissertation by MD Monjur Hossen, May 2005.
Poldermans B and Schoppink P, "Controlling the baking process and product quality with enzymes", Cereal Foods World, Mar. 1999, 44 (3), p. 132-135.
Leon et al., "A new approach to study starchy changes occurring the double-baking process and during bread storage," Z. Lebensn. Unters Forsch A, 1997, vol. 204 p. 316-320.
Aust K., Applications of lecithin in bakery foods, AIB Research Technical Bulletin, vol. XV, issue 12, Dec. 1993, p. 1-6.
Sommer et al., "Genetic and Biochemical Characterization of a new Extracellular Lipase from *Streptomyces cinnamomeus*," Applied Environmental Microbiology, 1997, vol. 63, No. 9, p. 3553-3560.
Glucose Oxidase, An Extract from the Enzyme Handbook, p. 1-7 (1995).
Kelley and Reddy, J. Bacteriology, vol. 166, p. 269-274 (1986).
Kelly and Reddy, Methods in Enzymology, vol. 161, p. 307-316 (1988).

(Continued)

*Primary Examiner* — Leslie Wong
(74) *Attorney, Agent, or Firm* — Steptoe & Johnson LLP

(57) ABSTRACT

A method of improving the rheological properties of a flour dough and the quality of the finished product made from such a dough, comprising adding an effective amount of an oxidoreductase capable of oxidizing maltose, in particular a hexose oxidase, e.g. isolated from an algal species such as *Iridophycus flaccidum*, *Chondrus crispus* or *Euthora cristata* and a dough improving composition comprising the oxidoreductase.

21 Claims, No Drawings

FOREIGN PATENT DOCUMENTS

| | | |
|---|---|---|
| CL | 1375-1992 | 11/1992 |
| CL | 1376-1992 | 9/1993 |
| CL | 1363-95 | 9/1994 |
| CL | 39483 | 9/1994 |
| CL | 875-95 | 6/1995 |
| CL | 1595-1994 | 4/1996 |
| CL | 875-1994 | 5/1996 |
| CL | 1363-1995 | 8/1996 |
| CN | 036151 | 2/2002 |
| CN | 172509 | 6/2003 |
| CN | 97181706.5 | 8/2003 |
| DE | A1050703 | 3/1956 |
| DE | 4301904 | 2/1994 |
| EP | 0010296 | 12/1982 |
| EP | 0214761 | 3/1987 |
| EP | 0238023 | 9/1987 |
| EP | 0260573 | 3/1988 |
| EP | 0305216 | 3/1989 |
| EP | B1-321-811 | 6/1989 |
| EP | B1-338-452 | 10/1989 |
| EP | A0468731 | 7/1991 |
| EP | 0468731 | 1/1992 |
| EP | 0396 162 | 1/1993 |
| EP | 0575133 | 12/1993 |
| EP | 0585988 | 3/1994 |
| EP | 0 682 116 | 11/1995 |
| EP | 0 758 377 | 11/1995 |
| EP | 0 375 102 | 4/1996 |
| EP | 1108360 | 6/2001 |
| EP | 1624047 | 2/2006 |
| EP | 1624047 | 10/2006 |
| GB | 2 264 429 | 9/1993 |
| GB | 2358784 | 8/2001 |
| GR | 980402483 | 10/1998 |
| JP | 73016612 | 12/1970 |
| JP | 48016612 | 5/1973 |
| JP | 05476892 | 6/1979 |
| JP | 60078529 | 5/1985 |
| JP | 59088040 | 1/1986 |
| JP | 61085158 | 4/1986 |
| JP | 62118883 | 7/1987 |
| JP | 03164127 | 7/1991 |
| JP | A92084848 | 3/1992 |
| JP | 04-200339 | 7/1992 |
| JP | 04207145 | 7/1992 |
| JP | 04207146 | 7/1992 |
| JP | 04-370055 | 12/1992 |
| JP | 1994000010444 | 5/1994 |
| JP | 06-296467 | 10/1994 |
| JP | 1994000010444 | 10/1994 |
| JP | A6296467 | 10/1994 |
| JP | 07-079687 | 3/1995 |
| JP | 7 274807 | 10/1995 |
| JP | 07274807 | 10/1995 |
| JP | 63068697 | 3/1998 |
| JP | 10155493 | 6/1998 |
| JP | 03164127 | 7/1999 |
| JP | 04207145 | 7/1999 |
| JP | 04207146 | 7/1999 |
| JP | 2003524286 | 6/2000 |
| JP | 7521525 | 8/2004 |
| NL | 99911638.7 | 11/2002 |
| WO | WO88/02775 | 4/1988 |
| WO | WO89/01032 | 2/1989 |
| WO | WO94/04035 | 3/1994 |
| WO | WOA9501727 | 1/1995 |
| WO | WO 95/09909 | 4/1995 |
| WO | WO95129996 | 11/1995 |
| WO | WO 96/09772 | 4/1996 |
| WO | WO 96/13580 | 5/1996 |
| WO | WO 96/28542 | 9/1996 |
| WO | WO 96/32472 | 10/1996 |
| WO | WO96/39851 | 12/1996 |
| WO | WO 97/41736 | 11/1997 |
| WO | WO9800029 | 1/1998 |
| WO | WO 98/14594 | 4/1998 |
| WO | WO9816112 | 4/1998 |
| WO | WO 98/18912 | 5/1998 |
| WO | WO9823162 | 6/1998 |
| WO | WO 9826057 A1 | 6/1998 |
| WO | WO98/31790 | 7/1998 |
| WO | WO98/45453 | 10/1998 |
| WO | WO99/31990 | 7/1999 |
| WO | WO00/32758 | 6/2000 |
| WO | WO00/75295 | 12/2000 |
| WO | WO01/39602 | 6/2001 |
| WO | WO02/00852 | 1/2002 |
| WO | WO02/03805 | 1/2002 |
| WO | WO02/065854 | 8/2002 |
| WO | WO02/066622 | 8/2002 |
| WO | 03/020941 | 3/2003 |
| WO | WO03/089620 | 10/2003 |
| WO | WO 2008/094847 | 8/2008 |

OTHER PUBLICATIONS

Giffhorn, Appl. Microbiol. Biotechnol., vol. 54, p. 727-740 (2000).
Kaplan, Methods in Enzymology, vol. 3, p. 107-110 (1957).
Smith and Whelan, Biochemical Preparations, vol. 10, p. 126-130 (1963).
Sen S. et al., Developments in Directed Evolution for Improving Enzyme Functions, Appl. Biochem. Biotechnol., 2007, vol. 143, No. 3, p. 212-223.
International Dairy Federation Bulletin Document, Document 116, p. 5. (1979).
Seffernick et al., Journal of Bacteriology, vol. 183, No. 8, p. 2405-2410 (2001).
Wirkowski et al., Biochemistry, vol. 38, No. 36, p. 11643-11650 (1999).
AOCS Introduction to the Processing of Fats and Oils, American Oil Chemists, p. III-16-III-19 (2003).
Chica et al., Current Opinion in Biotechnology, vol. 16, p. 378-384 (2005).
Garcia et al., Methods Enzymol., vol. 71, p. 782-772 (1981).
Sequence of enzyme GCAT (glycerophospholipidcholesterolacyltranspherase) (P10480, http://www.ncbi.nim.nih.gov/entrez/viewer.fcgi?db-protein&id=118-572649) (1989).
Verenium Corporation leaflet Purifine.RTM. Enzyme (Jan. 2008).
U.S. Appl. No. 10/040,394, filed Jan. 9, 2002.
U.S. Appl. No. 10/150,429, filed May 17, 2002.
U.S. Appl. No. 09/932,923, filed Aug. 21, 2001.
U.S. Appl. No. 09/824,053, filed Apr. 3, 2001.
Bean and Hassid, 1956, J. Biol. Chem. , 218: 425-436.
Ikawa, 1982, Methods Enzymol., 89: 145-149.
Sullivan et al., 1973, Biochemica et Biophysica Acta, 309:11-22.
Rand, 1972, Journal of Food Science, 37:698-701.
Bak et al., "A Method for Testing the Strengthening Effect of Oxidative Enzymes in Dough", presented at a symposium entitled "Wheat Structure, Biochemistry and Functionality", Reading UK, Apr. 10-12, 1995.
Christiansen, 1993, "Application of Oxidoreductases for Food Preservation" in Progress Report of R&D Projects and Concerted Actions published by the European Communities, Luxembourg, 1993, p. 32-36.
Kerschensteiner, The Mechanism of Action and the State of Copper in Hexose oxidase, Thesis, 1978, p. iii-xiii.
Perella, F.W., Analytical Biochemistry, 174:437-447 (1988).
AACC Method 36-01A.
"Enzyme Technology in Flour Milling and Baking", Baking Industry Europe (Alan Gordon, editor), S. Haarasilta and T. Pullinen (1993), pp. 49-52.
"Enzyme Nomenclature 1984 (Recommendations of the Nomenclature Committee of the International Union of Biochemistry on the Nomenclature and Classification of Enzyme-Catalysed Reactions)" (1984), pp. v, ix, and 50-51.
"Glucose Oxidase: Production, Properties, Present and Potential Applications", Soc. Chem. Ind. (Londen), (1961), L.A. Underkofler, p. 72-86.
"Methods in Enzymology", Biomass Part B Glucose Oxidase of Phanerochaete chrysosporium, R.L. Kelley and C.A. Reddy (1988), 161, pp. 306-317.
Definition of "hexose", Webster Dictionary, p. 1065.

"Baking Science & Technology", E.J. Pyler (1982), vol. 1, pp. 314-316.

"Novel Enzyme Combinations a New Tool to Improve Baking Results", Agro-Industry Hi-Tech, S. Haarasilta and T. Pullinen, (May/Jun. 1992), p. 12-13.

"Enzyme Nomenclature (Recommendations of the Nomenclature Committee of the International Union of Biochemistry and Molecular Biology on the Nomenclature and Classification of Enzymes)" (1992), p. 56.

"Enzyme Function", Experimental Report from Novo Nordisk, Mar. 13, 1997, 2 pages.

J. Chromatog., Knoll et al., 55 (1971), 425-428.

"DEEO.RTM." A glucose oxidase and catalase enzyme system product sheet from Miles laboratories—Enzymes from Miles (technical Information) (1976), 5 pages.

"Enzymes in Food Processing", 2.sup.nd Ed. By G. Reed, Universal Foods Corporation, Academic Press (1975), p. 222-229.

"Properties and Applications of the Fungal Enzyme Glucose Oxidase", reprinted from "Proceedings of the International Symposium on Enzyme Chemistry", Tokyo and Kyoto, (1957) L.A. Underkofler, (1958), pp. 486-490.

"The Oxidation of Glucose and Related Compounds by Glucose Oxidase from *Aspergillus niger*", Biochemistry, Pazur et al., vol. 3(4), 1964, 578-583.

"Technology of Cereals (with special reference to wheat)", 2.sup.nd Ed., Pergamom Press Ltd. N. L. Kent, (1975), pp. iv-v, 48-49, and 72-73.

"Gluzyme.TM." product sheet from Novo Nordisk Enzyme Process Division, Jan. 1994, 2 pages.

Derwent Publications Ltd., London, GB; AN 73-30288u XP002012361 & JP, A4801661 2 (EISAI Co. Ltd.).

Clare et al., 1991, Bio/Technology 9:455-460 [3].

Cregg et al., 1987, In: Biological Research on Industrial Yeast, vol. II, Stewart, G.G. et al. (Eds.), pp. 1-18 [4].

Fernandez et al., 1992, Analytical Biochemistry, 201:255-264 [5].

Pedersen et al., 1996, J. Biol. Chem. 271:2514-2522 [10].

Sahm et al., 1973, Eur. J. Biochem. 37:250-256 [12].

Tschopp et al., 1987, Bio/Technology 5:1305-1308 [17].

Barkholt, V. and A.L. Jensen, 1989, Amino Acid Analysis: Determination of Cysteine plus Half-Cysteine in Proteins after Hydrochloric Acid Hydrolysis with a Disulfide Compound as Additive, Analytical Biochemistry, 177:318-322.

Fernandez, J. et al., 1994, An Improved Procedure for Enzymatic Digestion of Polyvinylidene Difluoride-Bound Proteins for Internal Sequence Analysis, Analytical Biochemistry, 218:112-117.

Groppe, J.C. and Morse, D.E., 1993, Isolation of full-length RNA templates for reverse transcription from tissues rich in RNase and proteoglycans, Anal. Biochem., 210:337-343.

Kerschensteiner, D.A. and Klippenstein, D.A., 1978, Purification Mechanism and State of Copper in Hexose Oxidase, Federation Proceedings 37:1816 abstract.

Laemmli, U.K., 1970, Cleavage of structural Proteins during the Assembly of the Head of Bacteriophage T4, Nature (London), 227:680-685.

Schagger, H. and von Jagow, G., 1987, Tricine-Sodium Dodecyl Sulfate-Polyacrylamide Gel Electrophoresis for the Separation of Proteins in the Range from 1 to 100 kDa, Analytical Biochemistry 166:368-379.

Sock, Jr. and Rohringer, R., 1988, Activity Staining of Blotted Enzymes by Reaction Coupling with Transfer Membrane-Immobilized Auxiliary Enzymes, Analytical Biochemistry 171:310-319.

Yeh, K-W, Juang, R.H. and Su, J-C, A Rapid and efficient method for RNA isolation from plants with high carbohydrate content, Focus 13 (3):102-103, 1991.

Maes et al., Analytica Chimica Acta, 284 (1993) 281-290.

Sambrook, J., Fritsch, E.F. and Maniatis, T., 1989, Molecular Cloning, A Laboratory Manual 2.sup.nd Ed. Cold Spring Harbor Laboratory Press, Cold Spring Harbor, NY.

PCT International Search Report for PCT/DK96/00238, issued Apr. 11, 1996.

International Search Report from the International Searching Authority in PCT/DK96/00239 issued Sep. 11, 1996.

The Examiner's Report on Application for Patent of Invention (Chilean Application No. 939-96) and English translation thereof.

Dowling et al., "Hexose Oxidation by an enzyme system of *Malleomyces pseudomallei*", Journal of Bacteriology (1956) 72: 555-560.

Bean et al., "Carbohydrate Metabolism of Citrus Fruits", Journal of Biological Chemistry (1961) 236: 1235-1240.

Witteveen, C.F.B.: Thesis "Gluconate formation and polyol metabolism in *Aspergillus niger*" selected pages (1993).

AACC Method 54-10.

Eltman, George L.: "A Colorimetric Method for Determining Low Concentrations of Mercaptans", Archives of Biochemistry and Biophysics (1958) 74: 443-450.

U.S. Appl. No. 09/824,053, filed Jul. 12, 1996, entitled "Recombinant Hexose Oxidase, A Method of Producing Same and Use of Such Enzyme," Inventor(s): Peter Stougaard et al.

Poulsen, C., et al., "Purification and Characterization of a Hexose Oxidase with Excellent Strengthening Effects in Bread", Cereal Chem., 75(1):51-57 (1998).

"Effect of Different Hexose Oxidase and Other Oxide Reductases in Dough", Experimental Data Submitted by Applicants in European Counterpart Application 96917368.

Krog, N.J., "Dynamic and Unique Monoglycerides", Cereal Foods World, 24(1): 10-11 (1979).

Matos, A.R., et al., "A Novel Patatin-like Gene Stimulated by Drought Stress Encodes a Galactolipid Acyl Hydrolase", FEBS Letters, 491: 188-192 (2001).

Withers-Martinez, C., et al., "A Pancreatic Lipase with a Phospholipase A1 activity: Crystal Structure of a Chimerica Pancreatic Lipase-Related Protein 2 from Guinea Pig", Structure, 4(11): 1363-1374 (1996).

Cordle, R.A., "The Hydrophobic Surface of Colipase Influences Lipase Activity at an Oil-Water Interface", Journal of Lipid Research, 39: 1759-1767 (1998).

Sahsah, Y., et al., "Purification and Characterization of a Soluble Lipolytic Acylhydrolase from Cowpea (*Vigna unguiculata* L.) Leaves", Biochemica et Biophysica Acta, 1215: 66-73 (1994).

O'Sullivan, J., et al., "A Galactolipase Activity Associated with the Thylakoids of Wheat Leaves (*Triticum aestivum* L.)", J. Plant Physiol., 131:393-404 (1987).

Carriere, F., et al., "Pancreatic Lipase Structure-Function Relationships by Domain Exchange," Biochemistry, 36: 239-248 (1997).

Bomscheuer, U.T., "Lipase-Catalyzed Syntheses of Monoacylglycerols", Enzyme and Microbial Technology, 17: 578-586 (1995).

Hou, C.T., "pH Dependence and Thermostability of Lipases from Cultures from the ARS Culture Collection", Journal of Industrial Microbiology, 13:242-248 (1994).

Villeneuve, P., et al., "Lipase Specificities: Potential Application in Lipid Bioconversions", Inform, 8(6): 640-650 (1997).

Cammann, K., et al., "Chemical Sensors and Biosensors-Principles and Applications", Angew. Chem. Int. Ed. Engl., 30: 516-539 (1991).

Allen, R.M. et al., "Low-Level Electrochemical Detection of Glucose Oxidase and a Glucose Oxidase Conjugate", Biosensors and Bioelectronics, 10:621-631 (1995).

Wiseman, A., "Immobilization of Glucose Oxidase into Membranes as Sensors for Food Analysis", Elsevier Science Publishers, (1987).

Wilson, R., et al., "Glucose Oxidase: An Ideal Enzyme", Biosensors and Bioelectronics, 7:165-185 (1992).

Raba, J., et al., "Glucose Oxidase as an Analytical Reagent", Critical Reviews in Analytical Chemistry, 25(1):1-42 (1995).

Volc, J., et al., "Glucose-2 Oxidase Activity in Mycelial Cultures of Basidiomycetes", Folia Microbiol., 30:141-147 (1985).

Giffhorn, F., "Fungal Pyranose Oxidases: Occurrence, Properties and Biotechnical Applications in Carbohydrate Chemistry", Appl. Microbiol. Biotechnol., 54:727-740 (2000).

Certificate of Analysis for Maltose Monohydrate, SIGMA.

Lin, Shuen-Fuh et al., "Purification and Characterization of a Novel Glucooligosaccharide Oxidase from *Acremonium strictum* T1", Biochimica et Biophysica Acta, 1118:41-47 (1991).

Pazur, J.H., et al., "Comparison of the action of Glucoamylase and Glucosyltransferase on D-Glucose, Maltose, and Malto-Oligosaccharaides," Carbohydrate Research, 58:193-202 (1977).

Qi Si, J., "New Enzymes for the Baking Industry", Food Tech Europe, 3(1):60-64 (1996), Novo Nordisk Ferment Ltd.
Weipert, D., "Rheologie von Roggenteigen., II. Der Einflu.beta. der Enzyme unterschiedlicher Spezifität auf dzas rheologische Verhalten des Teiges", Getreide, Mehl Und Brot, 26(10):275-280 (1972); and English language translation of Abstract.
Nicolas, J., "Mise au Point sur l 'action d'enzymers d'oxydoreduction en technologie boulangere. La maturation des farines de ble tendre et le petrissage des pates", Ann. Technol. Agric., 28(4):445-468 (1979); and English language translation of Abstract.
Mine, Y., "Application of the Enzymatic Methods to the Determination of Contaminated Yolk in Egg White", Food Research International, 29(1):81-84 (1996).
Pub. No. 06-296467 (JP 6296467), Oct. 25, 1994, Section No. FFFFFF, vol. 94, No. 10, p. FFFFFF, FF, FFFF (FFFFFFFF) believed to be Patent Abstracts of Japan vol. 95, No. 001.
Patent Abstracts of Japan vol. 16, No. 528 (C-1001).
Marion Didier, et al., "Lipids, Lipid-Protein Interactions and the Quality of Baked Cereal Products," Interactions: The Keys to Cereal Quality, (ed. Hamer & Hoseney), Chapter 6, pp. 131-167 (1998).
Conference May 6-8, 1999 in Santorini, Greece, "Lipases & Lipids Structure, Function and Biotechnological Applications," Slides presented by Charlotte Poulsen.
C.H. Poulsen, et al., "Effect and Functionality of Lipases in Dough and Bread," The First European Symposium on Enzymes and Grain Processing, pp. 204-214 (1997).
D. Marion, et al., "Wheat Lipids and Lipid-Binding Proteins: Structure and Function," Wheat Structure Biochemistry and Functionality, ed. Scholfield JP), pp. 245-260 (1995).
"Unique Chance for Better Bread," Direct, A Newsletter from Danisco Ingredients, (1996).
Sullivan, James Denis Jr., Diss. Abstr. Int. B, 1973, 34(5), 1875, CAN 80: 105204 AN 1974: 105204 CAPLUS, "Purification and characterization of hexose oxidase from the red alga Chondrus crispus".
Groen, B. W., s De Vries, J. A. Duine (1997), Eu. J. Biochem., vol. 244, pp. 858-861, "Characterization of hexose from the red seaweed Chondrus crispus".
Wolff, A. M., O. C. Hansen, U. Poulsen, S. Madrid, P. Stougaard (2001), Protein Expression and Purification., vol. 22, pp. 189-199, "Optimization of the Production of Chondrus crispus Hexose Oxidase in Pichia pastoris".
Kerschensteiner, D. D. Diss. Abstr. Int. B 1978, 39(7), 3299, CAN 90: 117113 AN 1978:117113 CAPLUS, "The mechanism of action and the state of copper in hexose oxidase".
Chan and Wasserman, Cereal Chem. vol. 70(1), p. 22-26.
Chemistry Comes Alive-2001.
Danisco further experimentation with color photographs.
Danisco further experimentation "Effect on dough of HOX and GOX on maltose in dough".
Experiments by Danisco "A method of improving the properties of flour dough, a flour dough improving composition and improved food products" (Declaration of Jorn Born Soe).
Experiments by Danisco "Evaluation of enzyme of present invention in the production of German mischbrot" (Declaration of Jorn Born Soe).
Danisco further experimentation "Experiments on glucoligosaccharide oxidase (GO) from Acremonium".
Effect of different Hexose Oxidase.
Curriculum vitae—Jorn Born Soe.
Testing of Hexose Oxidase in Baking.
Amendment in response to Office Action dated Jan. 3, 1999.
Keilin et al., Biochem J (1948) vol. 24, p. 206-207.
Experiments by Novo in Appeal Statement.
Exhibit A filed by DSM.
Exhibit B filed by DSM.
Semashko et al., Applied Biochem and Microbiol. (2003), vol. 39, p. 368-374.
Garzillo et al., Biotechnol Appl Biochem (1995) vol. 22, p. 169-178 and Proof of date of publication of Garzillo et al.
Publication by Danisco.
Publication by Danisco II.
Investigation of Glucose Oxidase from Cladosporium oxysporum.
Publication by Danisco (extracts from WO 99/31990).
Publication by Danisco (Grindamyl SUREBake Bakery Enzymes).
Garcia et al. Journal of Agricultural and Food Chemistry (2004), vol. 52, p. 3946-3953.
Extract from Industrial Enzymology.
Glucose Oxidase: A much used and much loved enzyme in biosensors.
Glucose Oxidase (Gox) E.C. 1.1.3.4.
Enzyme Schemes.
Mancini (1995) Food Formulating.
Kulp K, Advances in Baking Technology, p. 152-178 (1993).
Danisco Experimentation "Effect of Alpha-Glucosidase on Gluconic Acid and Maltose."
Identification of alpha-glucosidase (otherwise known as transglucosidase) activity in Bakezyme GO 10000 from DSM.
Colombo, D. et al., Tetrahedron Letters, 1995. vol. 36, No. 27, pp. 4865-4868.
Bilyk, Journal of the American Oil Chemists' Society, 1991, vol. 68, No. 5, pp. 320-323.
Krupa, Z et al., Biochim Biophys Acta (1975), vol. 408(1), pp. 26-34.
Stryer, L., 1981, Biochemistry, 2.sup.nd ed, W.H. Freeman and Co., San Francisco.
Arskog and Joergensen, "Baking of prior art lipases from Candida cylindraceaa and Aspergillus foeditus and their activity on galactolipids on dough," Novozymes Report 2005.
Arskog and Joergensen, "Baking of prior art lipases from Humicola lanuginosea, Aspergillus tubigensis, Rhizopus delemar and Thizomucor miehei, and their activity on galactolipids on dough," Novozymes Report 2005.
Briand et al., "Lipids," Aug. 1995, vol. 30, No. 8, pp. 747-754.
Seino, H. et al., JAOCS, Nov. 1984, vol. 61, No. 11, pp. 1761-1765.
Al-Obaidy, K.A., Dissertation Abstracts International B (1987), vol. 47(9) 3597, order No. DA8624641, pp. 266.
Amano Enzymes, Armano Enzyme Europe Ltd, Sep. 1994.
Andersson, Lena, et al., Journal of Lipid Research (1995), vol. 36, pp. 1392-400.
Atsushi, Tsuchiya, et al., FEMS Microbiology Letters, vol. 143, pp. 63-67.
Carriere, F., et al., Biochim Biophys Acta, (1998), vol. 1376(3), pp. 417-432.
Chung, O.K., et al., Cereal Chemistry (1980), vol. 57(2), pp. 111-117.
Collar, C., et al., Lab de Cereales Inst de Agroquimica y Tec de Alimentos, CSIC, Food Science and Technology International 2001, vol. 7(6), pp. 501-510.
Drost-Lustenberger, C. and Spendler, T., Lipopan F BG—Application and Mechanism of a new lipase for baking, Novozymes, pp. 41-48.
Duan, Rui-Dong, Fat Digestion and Absorption (2000), pp. 25-46, publisher AOCS Press, Champaign III CODEN 69ACBA Conference; general review written in English.
Food Enzymes: Stalingase L, Gist-brocades Food Ingredients.
Functionality and mechanism of a new 2nd generation lipase for baking industry—Abstract 2001 AACC Annual Meeting: Symposia at Charlotte, NC Oct. 14-18, 2001.
Gemel, J., et al., Eur. J. Biochem. (1987), vol. 166(1), pp. 229-233.
Greenough, R.J., et al., Food and Chemical Toxicology, vol. 34(2), 1996, pp. 161-166.
Helmsing, P.J., Biochim Biophys Acta (1969), vol. 178(3), pp. 519-533.
Hirayama, O., et al., Biochim Biophys Acta. 1975, vol. 384(1), pp. 127-137.
Jacob, J.S., et al., The Journal of Cell Biology, vol. 103, 1986, pp. 1337-1347.
Kaniuga, Z, Acta Biochim Pol. (1997), vol. 4(1), pp. 21-35.
Kim, M.-J., et al., J Agric Food Chem (2001), vol. 49(5), pp. 2241-2248.
Kochubeil, S.M., et al., Biofizika (1981), vol. 26(2), pp. 295-304.
Kochubel, S.M., et al., Mol Biol (Mosk) (1975), (vol. 9(2), pp. 190-193), pp. 150-153.
Kochubel, S.M., et al., Mol Biol (Mosk) (1978) (vol. 12(1), pp. 47-54), pp. 32-37.
Krupa, Z., et al., Biochim Biophys Acta (1975), vol. 408(1), pp. 26-34.

Larsen, N.G., et al., Journal of Cereal Science (1990), vol. 12(2), pp. 155-164.

Lin, M.J.Y., et al., Cereal Chemistry (1974), vol. 51(1), 34-45.

Lipase A "Amano" 6 Assay Note, Amano Pharmaceutical Co Ltd Nagoya Japan, Aug. 27, 1985.

Lipase AP "Amano" 6 Assay Note and Produce Specification from Amano Pharmaceutical Co Ltd Nagoya Japan, Dec. 16, 1985.

Lipase SP677 as a Banking Enzyme, from Novo Nordisk, Denmark, Mar. 17, 1994.

Lipopan F: Keep the quality-cut your costs 2000 Novozymes A/S.

Luzi, P., et al., Genomics (1995), vol. 26(2), pp. 407-409.

Matos, A.R., et al., Lipid Catabolism: Lipid Degradation, 2000, pp. 779-781.

Matsuda, H., et al., Biochim Biophys Acta, (1979), vol. 573(1), pp. 155-165.

Michalski, W.P., et al., Biochim Biophys Acta (1980), vol. 589(1), pp. 84-99.

Mohsen, S.M., et al., Egypt J Food Sci, vol. 14(1), 1986, pp. 175-182.

Nierle, W., et al., Fette Seifen Anstrichmittel (1981), vol. 83(10), pp. 391-395.

Nobuloshi, Murakami, et al., Tetrahedron Letters (1991), vol. 32(10), pp. 1331-1334.

Ohm, J.B., et al., Cereal Chemistry (2002), vol. 79(2), pp. 274-278.

Ostrovskaya, L.K., et al., Dokl Akad Nauk SSSR, (vol. 186(4), 961-963), pp. 59-61.

Plijter, J. and Mutasers, JHGM, The surface rheological properties of dough and the influence of lipase on it, Gist-brocades, Bakery Ingredients Division, Oct. 1994.

Ponte, J.G., Cereal Chemistry (1969), vol. 46(3), pp. 325-329.

Poulsen, C., Effect and Functionality of Lipases in Dough and Bread, Angelino SAGF et al ed. The proceeding of the First European Symposium on Enzymes and Grain Processing. TNO Nutrition and Food Research Institute, Zeist, The Netherlands, 1997, pp. 200-214.

Product Description PD 40084-7a Grindamyl Exel 16 Bakery Enzyme, pp. 1-2.

Rousseau, D., et al., J Agric Food Chem., vol. 46(6), 1998, pp. 2375-2381.

Sahsah, Y., et al., Physiologia Planarum (1998), vol. 104(4), p. 577-586.

Sakai, N., et al., Biochimica et Biophysica Acta (1998), vol. 1395(1), pp. 62-67.

Sakaki, T., et al., Advanced Research on Plant Lipids, Proceedings of the International symposium on Plant Lipids, 15th, Okazaki, Japan, May 12-17, 2002 (2003), pp. 291-294, Publisher Kluwer Academic Publishers.

Sales Range for Banking Improver and Premix Manufacturers from DSM Bakery Ingredients.

Sequence alignment of database accession No. Q44268 (database: UNIProtKB/TrEMBL) with SEQ. ID No. 16.

Sequence alignment of database accession No. Q44268 (database: UNIProtKB/TrEMBL) with SEQ. ID No. 70.

Sias, B., et al., Biochemistry, (2004), vol. 43(31), pp. 10138-10148.

Strickland, James A., et al., Plant Physiol (1995), vol. 109, pp. 667-674.

Sztajer, H., et al., Acta Biotechnol, vol. 8, 1988, pp. 169-175.

Terasaki, M., et al., Biosci Biotechnol Biochem (2003), vol. 67(9), pp. 1986-1989.

The First European Symposium of Enzyme on Grain Processing—Proceedings, pp. 204-214.

\* cited by examiner

SEQUENCE LISTING

<160> NUMBER OF SEQ ID NOS: 1

<210> SEQ ID NO 1
<211> LENGTH: 19
<212> TYPE: PRT
<213> ORGANISM: Chondrus Crispus
<220> FEATURE:
<223> OTHER INFORMATION: Description of Sequence: peptide

<400> SEQUENCE: 1

Asp Pro Gly Tyr Ile Val Ile Asp Val Asn Ala Gly Thr Pro Asp Lys
 1               5                   10                  15

Pro Asp Pro

METHOD OF IMPROVING THE PROPERTIES OF A FLOUR DOUGH, A FLOUR DOUGH IMPROVING COMPOSITION AND IMPROVED FOOD PRODUCTS

This application is a continuation application of U.S. patent application Ser. No. 10/676,006, filed Oct. 2, 2003, now U.S. Pat. No. 7,931,924, which is a divisional application of U.S. patent application Ser. No. 09/932,923, filed Aug. 21, 2001, now U.S. Pat. No. 6,726,942, which is a continuation of U.S. patent application Ser. No. 08/676,186, filed Jul. 12, 19967, now U.S. Pat. No. 6,358,543, which is a national stage entry of International Application No. PCT/DK96/00239, filed Jun. 4, 1996 and which is a continuation-in-part of U.S. patent application Ser. No. 08/483,870, filed Jun. 7, 1995, abandoned, each of which is hereby incorporated by reference in its entirety.

FIELD OF INVENTION

The invention pertains to the provision of flour doughs having improved rheological properties and farinaceous food products having improved quality characteristics and it provides a maltose oxidizing oxidoreductase-containing composition capable of conferring such improved properties on doughs and finished food products made herefrom when it is added as a component to the doughs, and a method of preparing improved doughs and farinaceous food products.

TECHNICAL BACKGROUND AND PRIOR ART

The invention relates in particular to a method of providing flour doughs having improved rheological properties and to finished baked or dried products made from such doughs, which have improved textural, eating quality and dimensional characteristics.

In this connection, the "strength" or "weakness" of doughs is an important aspect of making farinaceous finished products from doughs, including baking. The "strength" or "weakness" of a dough is primarily determined by its content of protein and in particular the content and the quality of the gluten protein is an important factor in that respect. Flours with a low protein content is generally characterized as "weak". Thus, the cohesive, extensible, rubbery mass which is formed by mixing water and weak flour will usually be highly extensible when subjected to stress, but it will not return to its original dimensions when the stress is removed.

Flours with a high protein content are generally characterized as "strong" flours and the mass formed by mixing such a flour and water will be less extensible than the mass formed from a weak flour, and stress which is applied during mixing will be restored without breakdown to a greater extent than is the case with a dough mass formed from a weak flour. Strong flour is generally preferred in most baking contexts because of the superior rheological and handling properties of the dough and the superior form and texture qualities of the finished baked or dried products made from the strong flour dough.

Doughs made from strong flours are generally more stable. Stability of a dough is one of the most important characteristics of flour doughs. According to American Association of Cereal Chemists (AACC) Method 36-01A the term "stability" can be defined as "the range of dough time over which a positive response is obtained and that property of a rounded dough by which it resists flattening under its own weight over a course of time". According to the same method, the term "response" is defined as "the reaction of dough to a known and specific stimulus, substance or set of conditions, usually determined by baking it in comparison with a control"

Within the bakery and milling industries it is known to use dough "conditioners" to strengthen the dough. Such dough conditioners are normally non-specific oxidizing agents such as eg iodates, peroxides, ascorbic acid, K-bromate or azodicarbonamide and they are added to dough with the aims of improving the baking performance of flour to achieve a dough with improved stretchability and thus having a desirable strength and stability. The mechanism behind this effect of oxidizing agents is that the flour proteins, in particular gluten contains thiol groups which, when they become oxidized, form disulphide bonds whereby the protein forms a more stable matrix resulting in a better dough quality and improvements of the volume and crumb structure of the baked products.

In addition to the above usefulness of ascorbic acid/ascorbate as a dough conditioner due to its oxidizing capacity, these compounds may also act as substrate for an oxidoreductase, ascorbate oxidase which is disclosed in EP 0 682 116 A1. In the presence of its substrate, this enzyme converts ascorbic acid/ascorbate to dehydroascorbic acid and $H_2O_2$. This prior art does not suggest that ascorbic acid oxidase in the presence of ascorbic acid/ascorbate might have a dough conditioning effect, but assumingly this is the case.

However, the use of several of the currently available oxidizing agents is either objected to by consumers or is not permitted by regulatory bodies and accordingly, it has been attempted to find alternatives to these conventional flour and dough additives and the prior art has i.a. suggested the use of glucose oxidase for this purpose.

Thus, U.S. Pat. No. 2,783,150 discloses the addition of glucose oxidase to flour to improve dough strength and texture and appearance of baked bread.

CA 2,012,723 discloses bread improving compositions comprising cellulolytic enzymes such as xylanases and glucose oxidase, the latter enzyme being added to reduce certain disadvantageous effects of the cellulolytic enzymes (reduced dough strength and stickiness) and it is disclosed that addition of glucose to the dough is required to obtain a sufficient glucose oxidase activity.

JP-A-92-084848 suggests the use of a bread improving composition comprising glucose oxidase and lipase.

EP-B1-321 811 discloses the use of an enzyme composition comprising sulfhydryl oxidase and glucose oxidase to improve the rheological characteristics of doughs. It is mentioned in this prior art document that the use of glucose oxidase alone has not been successful.

In EP-B1-338 452 is disclosed an enzyme composition for improving dough stability, comprising a mixture of cellulase/hemicellulase, glucose oxidase and optionally sulfhydryl oxidase.

However, the use of glucose oxidase as a dough improving additive has the limitation that this enzyme requires the presence of sufficient amounts of glucose as substrate in order to be effective in a dough system and generally, the glucose content in cereal flours is low. Therefore, the absence of glucose in doughs or the low content hereof in doughs will be a limiting factor for the effectiveness of glucose oxidase as a dough improving agent.

In contrast hereto, the content of maltose in cereal flours is generally significantly higher than that of glucose and accordingly, a freshly prepared dough will normally contain more maltose than glucose. Thus, in an experiment where the content of sugars in supernatants from suspensions of wheat flour and a dough prepared from the flour and further comprising water, yeast, salt and sucrose (as described in the following example 2.3) were analyzed, the following values (% by weight calculated on flour) were found:

|  | Flour | Dough |
| --- | --- | --- |
| Sucrose | 0.3 | <0.01 |
| Galactose | 0.001 | 0.01 |
| Glucose | 0.25 | 0.72 |
| Maltose | 2.6 | 1.4 |
| Fructose | 0.08 | 0.67 |
| Lactose | <0.01 | <0.01 |

In addition, the content of maltose remains at a relatively high level in a dough which is leavened by yeast, since the yeast primarily utilizes glucose, or it may even increase in the dough e.g. during proofing due to the activity of starch degrading enzymes such as e.g. β-amylase, which is inherently present in the flour or is added to the dough.

Whereas the prior at has recognized the useful improving effects of glucose oxidase on the rheological characteristics of bread doughs and on the quality of the corresponding baked products, it has also been realized that the use of this enzyme has several drawbacks. Thus, it may be required to add sucrose or glucose as substrate to the dough to obtain a sufficient effect and glucose oxidase does not constantly provide a desired dough or bread improving effect when used alone without the addition of other enzymes.

However, it has now been found that the addition of an oxido-reductase, which is capable of oxidizing maltose, including hexose oxidase as a sole dough conditioning agent, i.e. without concomitant addition of substrate for the added enzyme, or of other enzymes, to a farinaceous dough results in an increased resistance hereof to breaking when the dough is stretched, i.e. this enzyme confers in itself to the dough an increased strength whereby the dough becomes less prone to mechanical deformation. It is contemplated that this effect of addition of hexose oxidase to a dough is the result of the formation of cross-links between thiol grouts in sulphur-containing amino acids in wheat gluten which occurs when the $H_2O_2$ generated by the enzyme in the dough reacts with the thiol groups which are hereby oxidized.

Hexose oxidase (D-hexose:$O_2$-oxidoreductase, EC 1.1.3.5) is an enzyme which in the presence of oxygen is capable of oxidizing D-glucose and several other reducing sugars including maltose, glucose, lactose, galactose, xylose, arabinose and cellobiose to their corresponding lactones with subsequent hydrolysis to the respective aldobionic acids. Accordingly, hexose oxidases differ from glucose oxidase which can only convert D-glucose, in that hexose oxidases can utilize a broader range of sugar substrates. The oxidation catalyzed by the enzyme can be illustrated as follows:

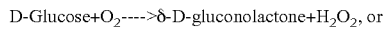

D-Glucose+$O_2$----> δ-D-gluconolactone+$H_2O_2$, or

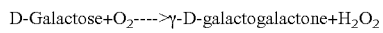

D-Galactose+$O_2$----> γ-D-galactogalactone+$H_2O_2$

Hexose oxidase (in the following also referred, to as HOX) has been isolated from several red algal species such as *Iridophycus flaccidum* (Bean and Hassid, 1956, J. Biol. Chem., 218:425-436) and *Chondrus crispus* (Ikawa 1982, Methods Enzymol., 89:145-149). Additionally, the algal species *Euthora cristata* (Sullivan et al. 1973, Biochemica et Biophysica Acta, 309:11-22) has been shown to produce HOX.

Other potential sources of hexose oxidase according to the invention include microbial species or land-growing plant species. Thus, as an example of such a plant source, Bean et al., Journal of Biological Chemistry (1961) 236: 1235-1240, have disclosed an oxidoreductase from citrus fruits which is capable of oxidizing a broad range of sugars including D-glucose, D-galactose, cellobiose, lactose, maltose, D-2-deoxyglucose, D-mannose, D-glucosamine and D-xylose. Another example of an enzyme having hexose oxidase activity is the enzyme system of *Malleomyces mallei* disclosed by Dowling et al., Journal of Bacteriology (1956) 72:555-560.

It has been reported that hexose oxidase isolated from the above natural sources may be of potential use in the manufacturing of certain food products. Thus, hexose oxidase isolated from *Iridophycus flaccidum* has been shown to be capable of converting lactose in milk with the production of the corresponding aldobionic acid and has been shown to be of potential interest as an acidifying agent in milk, e.g. to replace acidifying microbial cultures for that purpose (Rand, 1972, Journal of Food Science, 37:698-701). In that respect, hexose oxidase has been mentioned as a more interesting enzyme than glucose oxidase, since this latter enzyme can only be enzymatically effective in milk or other food products not containing glucose or having a low content of glucose, if glucose or the lactose-degrading enzyme lactase which convert the lactose to glucose and galactose, is also added.

The capability of oxidoreductases including that of hexose oxidase to generate hydrogen peroxide has also been utilized to improve the storage stability of certain food products including cheese, butter and fruit juice as it is disclosed in JP-B-73/016612. It has also been suggested that oxido-reductases may be potentially useful as antioxidants in food products.

However, the present invention has demonstrated that hexose oxidase is highly useful as a dough conditioning agent in the manufacturing of flour dough products including not only bread products but also other products made from flour doughs such as noodles and alimentary paste products.

SUMMARY OF THE INVENTION

Accordingly, the invention relates in a first aspect to a method of improving the rheological properties of a flour dough and the quality of the finished product made from the dough, comprising adding to the dough ingredients, dough additives or the dough an effective amount of an oxidoreductase which at least is capable of oxidizing maltose, such as e.g. a hexose oxidase.

In a further aspect, there is also provided a dough improving composition comprising an oxidoreductase which at least is capable of oxidizing maltose, and at least one further dough ingredient or dough additive.

In still further aspects, the invention pertains to a method of preparing a bakery product, comprising preparing a flour dough including adding an effective amount of an oxidoreductase which at least is capable of oxidizing maltose and baking the dough, and a method of preparing a dough-based food product comprising adding to the dough an effective amount of a maltose oxidizing oxidoreductase.

DETAILED DISCLOSURE OF THE INVENTION

In one aspect, the present method contemplates a method of improving the rheological properties of flour doughs. The method comprises, as it is mentioned above, the addition of an effective amount of a maltose oxidizing oxidoreductase either to a component of the dough recipe or to the dough resulting from mixing all of the components for the dough. In the present context, "an effective amount" is used to indicate that the amount is sufficient to confer to the dough and/or the finished product improved characteristics as defined herein.

In one useful embodiment of the method according to the invention, the oxidoreductase is a hexose oxidase. Hexose oxidase can, as it is described in details herein, be isolated from marine algal species naturally producing that enzyme. Such species are found in the family Gigartinaceae which belong to the order *Gigartinales*. Examples of hexose oxidase producing algal species belonging to Gigartinaceae are *Chondrus crispus* and *Iridophycus flaccidum*. Also algal species of the order *Cryptomeniales* including the species *Euthora cristata* are potential sources of hexose oxidase.

When using such natural sources for hexose oxidase, the enzyme is typically isolated from the algal starting material by extraction using an aqueous extraction medium. As starting material may be used algae in their fresh state as harvested from the marine area where they grow, or the algal material can be used for extraction of hexose oxidase after drying the fronds e.g. by air-drying at ambient temperatures or by any appropriate industrial drying method such as drying in circulated heated air or by freeze-drying. In order to facilitate the subsequent extraction step, the fresh or dried starting material may advantageously be comminuted e.g. by grinding or blending.

As the aqueous extraction medium, buffer solutions e.g. having a pH in the range of 5-8, such as 0.1 M sodium phosphate buffer, 20 mM triethanolamine buffer or 20 mM Tris-HCl buffer are suitable. The hexose oxidase is typically extracted from the algal material by suspending the starting material in the buffer and keeping the suspension at a temperature in the range of 0-20° C. such as at about 5° C. for 1 to 5 days, preferably under agitation.

The suspended algal material is then separated from the aqueous medium by an appropriate separation method such as filtration, sieving or centrifugation and the hexose oxidase is subsequently recovered from the filtrate or supernatant. Optionally, the separated algal material is subjected to one or more further extraction steps.

Since several marine algae contain coloured pigments such as phycocyanins, it may be required to subject the filtrate or supernatant to a further purification step whereby these pigments are removed. As an example, the pigments may be removed by treating the filtrate or supernatant with an organic solvent in which the pigments are soluble and subsequently separating the solvent containing the dissolved pigments from the aqueous medium. Alternatively, pigments may be removed by subjecting the filtrate or supernatant to a hydrophobic interaction chromatography step.

The recovery of hexose oxidase from the aqueous extraction medium is carried out by any suitable conventional methods allowing isolation of proteins from aqueous media. Such methods, examples of which will be described in details in the following, include conventional methods for isolation of proteins such as ion exchange chromatography, optionally followed by a concentration step such as ultrafiltration. It is also possible to recover the enzyme by adding substances such as e.g. $(NH_4)_2SO_4$ or polyethylene glycol (PEG) which causes the protein to precipitate, followed by separating the precipitate and optionally subjecting it to conditions allowing the protein to dissolve.

For certain applications of hexose oxidase it is desirable to provide the enzyme in a substantially pure form e.g. as a preparation essentially without other proteins or non-protein contaminants and accordingly, the relatively crude enzyme preparation resulting from the above extraction and isolation steps may be subjected to further purification steps such as further chromatography steps, gel filtration or chromatofocusing as it will also be described by way of example in the following.

In a preferred embodiment of the method according to the invention, a flour dough is prepared by mixing flour with water, a leavening agent such as yeast or a conventional chemical leavening agent, and an effective amount of hexose oxidase under dough forming conditions. It is, however, within the scope of the invention that further components can be added to the dough mixture.

Typically, such further dough components include conventionally used dough components such as salt, a sweetening agent such as sugars, syrups or artificial sweetening agents, lipid substances including shortening, margarine, butter or an animal or vegetable oil and one or more dough additives such as emulsifying agents, starch degrading enzymes, cellulose or hemicellulose degrading enzymes, proteases, lipases, non-specific oxidizing agents such as those mentioned above, flavouring agents, lactic acid bacterial cultures, vitamins, minerals, hydrocolloids such as alginates, carrageenans, pectins, vegetable gums including e.g. guar gum and locust bean gum, and dietary fiber substances.

Conventional emulsifiers used in making flour dough products include as examples monoglycerides, diacetyl tartaric acid esters of mono- and diglycerides of fatty acids, and lecithins e.g. obtained from soya. Among starch degrading enzymes, amylases are particularly useful as dough improving additives. α-amylase breaks down starch into dextrins which are further broken down by β-amylase into maltose. Other useful starch degrading enzymes which may be added to a dough composition include glucoamylases and pullulanases. In the present context, further interesting enzymes are xylanases and other oxidoreductases such as glucose oxidase, pyranose oxidase and sulfhydryl oxidase.

A preferred flour is wheat flour, but doughs comprising flour derived from other cereal species such as from rice, maize, barley, rye and durra are also contemplated.

The dough is prepared by admixing flour, water, the oxidoreductase according to the invention and other possible ingredients and additives. The oxidoreductase can be added together with any dough ingredient including the water or dough ingredient mixture or with any additive or additive mixture. The dough can be prepared by any conventional dough preparation method common in the baking industry or in any other industry making flour dough based products.

The oxidoreductase can be added as a liquid preparation or in the form of a dry powder composition either comprising the enzyme as the sole active component or in admixture with one or more other dough ingredients or additive. The amount of the enzyme component added normally is an amount which results in the presence in the finished dough of 1 to 10,000 units per kg of flour, preferably 5 to 5000 units such as 10 to 1000 units. In useful embodiments, the amount is in the range of 20 to 500 units per kg of flour. In the present context 1 oxidoreductase unit corresponds to the amount of enzyme which under specified conditions results in the con-version of 1 μmole glucose per minute. The activity is stated as units per g of enzyme preparation.

The effect of the oxidoreductase on the rheological properties of the dough can be measured by standard methods according to the International Association of Cereal Chemistry (ICC) and the American Association of Cereal Chemistry (AACC) including the amylograph method (ICC 126), the farinograph method (AACC 54-21) and the extensigraph method (AACC 54-10). The extensigraph method measures e.g. the dough's ability to retain gas evolved by yeast and the ability to withstand proofing. In effect, the extensigraph method measures the relative strength of a dough. A strong dough exhibits a higher and, in some cases, a longer extensigraph curve than does a weak dough. AACC method 54-10 defines the extensigraph in the following manner: "the extensigraph records a load-extension curve for a test piece of dough until it breaks. Characteristics of load-extension curves or extensigrams are used to assess general quality of flour and its responses to improving agents".

In a preferred embodiment of the method according to the invention, the resistance to extension of the dough in terms of the ratio between the resistance to extension (height of curve, B) and the extensibility (length of curve, C), i.e. the B/C ratio as measured by the AACC method 54-10 is increased by at least 10% relative to that of an otherwise similar dough not containing oxidoreductase. In more preferred embodiments, the resistance to extension is increased by at least 20%, such as at least 50% and in particular by at least 100%.

The method according to the invention can be used for any type of flour dough with the aims of improving the rheological properties hereof and the quality of the finished products made from the particular type of dough. Thus, the method is highly suitable for the making of conventional types of yeast leavened bread products including wheat flour based bread products such as loaves and rolls. However, it is contemplated that the method also can improve the properties of doughs in which leavening is caused by the addition of chemical leavening agents, including sweet bakery products such as cake products including as examples pound cakes and muffins, or scones.

In one interesting aspect, the invention is used to improve the rheological properties of doughs intended for noodle products including "white noodles" and "chinese noodles" and to improve the textural qualities of the finished noodle products. A typical basic recipe for the manufacturing of noodles comprises the following ingredients: wheat flour 100 parts, salt 0.5 parts and water 33 parts. The noodles are typically prepared by mixing the ingredients in an appropriate mixing apparatus followed by rolling out the noodle dough using an appropriate noodle machine to form the noodle strings which are subsequently air dried.

The quality of the finished noodles is assessed e.g. by their colour, cooking quality and texture. The noodles should cook as quickly as possible, remain firm after cooking and should preferably not loose any solids to the cooking water. On serving the noodles should preferably have a smooth and firm surface not showing stickiness and provide a firm "bite" and a good mouthfeel. Furthermore, it is important that the noodles have a light colour.

Since the appropriateness of wheat flour for providing noodles having the desired textural and eating qualities may vary according to the year and the growth area, it is usual to add noodle improvers to the dough in order to compensate for sub-optimal quality of the flour. Typically, such improvers will comprise dietary fiber substances, vegetable proteins, emulsifiers and hydrocolloids such as e.g. alginates, carrageenans, pectins, vegetable gums including guar gum and locust bean gum, and amylases.

It has been attempted to use glucose oxidase as a noodle improving agent. However, as mentioned above, the content of glucose may be so low in wheat flour that this enzyme will not be effective.

It is therefore an important aspect of the invention that the oxidoreductase according to the invention is useful as a noodle improving agent, optionally in combination with other components currently used to improve the quality of noodles. Thus, it is contemplated that noodles prepared in accordance with the above method will have improved properties with respect to colour, cooking and eating qualities including a firm, elastic and non-sticky texture and consistency.

In a further useful embodiment the dough which is prepared by the method according to the invention is a dough for preparing an alimentary paste product. Such products which include as examples spaghetti and macaroni are typically prepared from a dough comprising as the main ingredients flour and eggs. After mixing of the ingredient, the dough is formed to the desired type of paste product and air dried. It is contemplated that the addition to a paste dough will have a significant improving effect on the extensibility and stability hereof resulting in finished paste product having improved textural and eating qualities.

In a further aspect of the invention there is provided a dough improving composition comprising the oxidoreductase according to the invention and at least one further dough ingredient or dough additive.

In a preferred embodiment, the oxidoreductase is hexose oxidase. The further ingredient or additive can be any of the ingredients or additives which are described above. The composition may conveniently be a liquid preparation comprising the oxidoreductase. However, the composition is conveniently in the form of dry composition. It will be understood that the amount of oxidoreductase activity in the composition will depend on the types and amounts of the further ingredients or additives. However, the amount of oxidoreductase activity is preferably in the range of 10 to 100,000 units, preferably in the range of 100 to 50,000 units such as 1,000 to 10,000 units including 2,000 to 5,000 units.

Optionally, the composition may be in the form of a complete dough additive mixture or pre-mixture for a making a particular finished product and containing all of the dry ingredients and additives for such a dough. In specific embodiments, the composition may be one particularly useful for preparing a baking product or in the making of a noodle product or an alimentary paste product.

As mentioned above, the present invention provides a method for preparing a bakery product including the addition to the dough of an oxidoreductase such as e.g. hexose oxidase. In particular, this method results in bakery products such as the above mentioned products in which the specific volume is increased relative to an otherwise similar bakery product, prepared from a dough not containing oxidoreductase. In this context, the expression "specific volume" is used to indicate the ratio between volume and weight of the product. It has surprisingly been found that in accordance with the above method, the specific volume can be increased significantly such as by at least 10%, preferably by at least 20%, including by at least 30%, preferably by at least 40% and more preferably by at least 50%.

In one advantageous embodiment of the above method at least one further enzyme is added to the dough. Suitable examples hereof include a cellulase, a hemicellulase, a xylanase, a starch degrading enzyme, a glucose oxidase, a lipase and a protease.

The invention will now be described by way of illustration in the following non-limiting examples.

Example 1

1.1. Purification of Hexose Oxidase from *Chondrus crispus*

A purified hexose oxidase preparation was obtained using the below extraction and purification procedures. During these procedures and the following characterizations of the purified enzyme, the following assay for determination of hexose oxidase activity was used:

1.1.1. Assay of Hexose Oxidase Activity

The assay was based on the method described by Sullivan and Ikawa (Biochimica et Biophysica Acta, 1973, 309:11-22), but modified to run in microtiter plates. An assay mixture contained 150 µl β-D-glucose (0.1 M in 0.1 M sodium phosphate buffer, pH 6.3), 120 µl 0.1 M sodium phosphate buffer, pH 6.3, 10 µl o-dianisidine-dihydrochloride (Sigma D-3252, 3.0 mg/ml in $H_2O$), 10 µl peroxidase (POD) (Sigma P-8125, 0.1 ml in 0.1 M sodium phosphate buffer, pH 6.3) and 10 µl enzyme (HOX) solution. Blanks were made by adding buffer in place of enzyme solution.

The incubation was started by the addition of glucose. After 15 minutes of incubation at 25° C. the absorbance at 405 nm was read in an ELISA reader. A standard curve was constructed using varying concentrations of $H_2O$, in place of the enzyme solution.

The reaction can be described in the following manner:

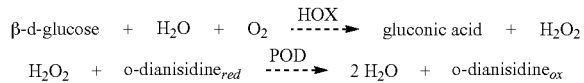

Oxidized o-dianisidine has a yellow colour absorbing at 405 nm.

1.1.2. Extraction

Fresh *Chondrus crispus* fronds were harvested along the coast of Brittany, France. This fresh material was homogenized in a pin mill (Alpine). To a 100 g sample of the resulting homogenized frond material was added 300 ml of 0.1 M sodium phosphate buffer, pH 6.8. The mixture was subsequently sonicated in a sonication bath for 5 minutes and then extracted under constant rotation for 4 days at 5° C., followed by centrifugation of the mixture at 47,000×g for 20 minutes.

300 ml of the resulting clear pink supernatant was desalted by ultrafiltration using an Amicon ultrafiltration unit equipped with an Omega (10 kD cut off, Filtron) ultrafiltration membrane.

1.1.3. Anion Exchange Step

The retentate resulting from 1.1.2 was applied to a 5×10 cm column with 200 ml Q-Sepharose FF equilibrated in 20 mM triethanolamine, pH 7.3. The column was washed with the equilibration buffer and hexose oxidase eluted with a 450 ml gradient of 0 to 1 M of NaCl in equilibration buffer. The column was eluted at 6 ml/minute, and fractions of 14 ml collected. Fractions 9-17 (total 125 ml) were pooled and concentrated by ultrafiltration using an Amicon 8400 unit equipped with an Omega (10 kD cut off, Filtron) ultrafiltration membrane to 7.3 ml.

1.1.4 Gel Filtration

The above 7.5 ml retentate was applied to a Superdex 200 2.6×60 cm gel filtration column equilibrated in 50 mM sodium phosphate buffer, pH 6.4 and eluted at a flow rate of 1 ml/-minute. Fractions of 4 ml were collected. Fractions 17-28 (total volume 50 ml) containing the hexose oxidase activity were pooled.

1.1.5. Hydrophobic Interaction Chromatography

To the pool resulting from the gel filtration step 1.1.4 ammonium sulphate was added to a final concentration of 2 M. This mixture was then applied to a 1.6×16 cm column with 32 ml phenyl sepharose equilibrated in 20 mM sodium phosphate buffer, pH 6.3 and 2 M $(NH_4)_2SO_4$. The column was washed with equilibration buffer followed by elution of hexose oxidase at a flow rate of 2 ml/minute using a 140 linear gradient from 2 M to 0 M $(NH_4)_2SO_4$ in 20 mM sodium phosphate buffer. Fractions of 4 ml were collected and fractions 24-33 containing the hexose oxidase activity were pooled.

The above mentioned pink colour accompanies the enzyme, but it is separated from hexose oxidase in this purification step.

1.1.6. Mono Q Anion Exchange

The above pool resulting from the above phenyl sepharose chromatography step was desalted by ultrafiltration as described above. 2 ml of this pool was applied to a Mono Q HR 5/5 column equilibrated in 20 mM triethanolamine, pH 7.3. The column was subsequently eluted using a 45 ml linear gradient from 0 to 0.65 M NaCl in equilibration buffer at a flow rate 1.5 ml/minute. Fractions of 1.5 ml were collected and fractions 14-24 were pooled.

1.1.7 Mono P Anion Exchange

The hexose oxidase-containing pool from the above step 1.1.6 was applied to a Mono P HR 5/5 column equilibrated in 20 mM bis-Tris buffer, pH 5.5. The enzyme was eluted using a 45 ml linear gradient from 0 to 0.65 M NaCl in equilibration buffer at a flow rate of 1.5 ml/minute, and fractions of 0.75 ml were collected. The highest hexose oxidase activity was found in fraction 12.

1.2. Characterization of the Purified Hexose Oxidase

The hexose oxidase-containing pools from the above steps 1.1.6 and 1.1.7 were used in the below characterization experiments:

1.2.1. Determination of Molecular Weight

The size of the purified native hexose oxidase was determined by gel permeation chromatography using a Superose 6 HR 10/30 column at a flow rate of 0.5 ml/minute in 50 mM sodium phosphate buffer, pH 6.4. Ferritin (440 kD), catalase (232 kD), aldolase (158 kD), bovine serum albumin (67 kD) and chymotrypsinogen (25 kD) were used as size standards. The molecular weight of the purified hexose oxidase was determined to be 120±10 kD.

1.2.2. Determination of pH Optimum

Assay mixtures for the determination of pH optimum (final volume 300 µl) contained 120 µl of 0.1 M stock solution of sodium phosphate/citrate buffer of varying pH values. All other assay mixture components were dissolved in $H_2O$. The pH was determined in the diluted stock buffer solutions at 25° C.

The hexose oxidase showed enzymatic activity from pH 3 to pH 8, but with optimum in the range of 3.5 to 5.5.

1.2.3. $K_m$ of the Hexose Oxidase for Glucose and Maltose, Respectively

Kinetic data were fitted to $v=V_{max}S/(K_m+S)$, where $V_{max}$ is the maximum velocity, S is the substrate concentration and $K_m$ is the concentration giving 50% of the maximum rate (Michaelis constant) using the EZ-FIT curve fitting microcomputer programme (Perrella, F. W., 1988, Analytical Biochemistry, 174:437-447).

A typical hyperbolic saturation curve was obtained for the enzyme activity as a function of glucose and maltose, respectively. $K_m$ for glucose was calculated to be 2.7 mM±0.7 mM and for maltose the $K_m$ was found to be 43.7±5.6 mM.

Example 2

Dough Improving Effect of Hexose Oxidase Extracted from *Chondrus crispus*

2.1. Purification of Hexose Oxidase from *Chondrus crispus*

For this experiment, hexose oxidase was prepared in the following manner:

Fresh *Chondrus crispus* material was collected at the coast of Brittany, France. The material was freeze-dried and subsequently ground. 40 g of this ground material was suspended in 1000 ml of 20 mM triethanolamine (TEA) buffer, pH 7.3 and left to stand at 5° C. for about 64 hours with gentle agitation and then centrifuged at 2000×g for 10 minutes. The supernatant was filtered through GF/A and GF/C glass filters followed by filtering through a 45 μm pore size filter to obtain a filtrate preparation of 800 ml having hexose oxidase activity corresponding to a glucose oxidase activity of 0.44 units per g of preparation. The activity was determined using the below procedure.

The supernatant was applied onto a 330 ml bed volume chromatographic column with anionic exchange Q Sepharose Big Beads (dead volume 120 ml). The bound proteins were eluted over 180 minutes using a gradient from 0 to 0.5 M NaCl in 20 mM TEA buffer, pH 7.3 followed by 1 M NaCl in 20 mM TEA buffer, and fractions of 9 ml were collected and analyzed for hexose oxidase activity using the below analytical procedure.

Hexose oxidase activity-containing fractions 60-83 were pooled (about 250 ml) and concentrated and desalted by ultrafiltration to about 25 ml. This step was repeated twice on the retentates to which was added 100 ml 0.05 mM TEA. The resulting retentate of 25 ml contained 0.95 glucose oxidase activity units per g.

2.2. Determination of Glucose Oxidase Activity

Definition: 1 glucose oxidase (GOD) unit corresponds to the amount of enzyme which under the specified conditions results in the conversion of 1 μmole glucose per min. The activity is stated as units per g of enzyme preparation.

Reagents: (i) Buffer: 20 g $Na_2HPO_4$-$2H_2O$ is dissolved in 900 ml distilled water, pH is adjusted to 6.5; (ii) dye reagent (stock solution): 200 mg of 2,6-dichloro-phenol-indophenol, Sigma No. D-1878 is dissolved in 1000 ml distilled water under vigorous agitation for 1 hour; (iii) peroxidase (stock solution): Boehringer Mannheim No. 127 361, 10,000 units is dissolved in 10 ml distilled water and 4.2 g of ammonium sulphate added; (iv) substrate: 10% w/v D-glucose solution in buffer, (v) standard enzyme: hydrase #1423 from Amano.

Analytical principle and procedure: Glucose is converted to gluconic acid and $H_2O_2$ which is subsequently converted by peroxidase to $H_2O$ and $O_2$. The generated oxygen oxidizes the blue dye reagent 2,6-dichloro-phenol-indophenol which thereby changes its colour to purple. The oxidized colour is measured spectrophotometrically at 590 nm and the enzymatic activity values calculated relative to a standard.

2.3. The Effect of the Hexose Oxidase Preparation on Cross-Linking Between Thiol Groups in a Wheat Flour Based Dough The effect of hexose oxidase on the formation of thiol group cross-linking was studied by measuring the content of free thiol groups in a dough prepared from 1500 g of wheat flour, 400 Brabender Units (BU) of water, 90 g of yeast, 20 g of sucrose and 20 g of salt to which was added 0, 100, 250, 875 and 1250 units per kg of flour, respectively of the above hexose oxidase preparation. The measurement was carried out essentially in accordance with the colorimetric method of Ellman (1958) as also described in Cereal Chemistry, 1983, 70, 22-26. This method is based on the principle that 5.5'-dithio-bis(2-nitrobenzoic acid) (DTNB) reacts with thiol groups in the dough to form a highly coloured anion of 2-nitro-5-mercapto-benzoic acid, which is measured spectrophotometrically at 412 nm.

Assuming that the relative change of the amount of thiol groups in a dough is reflected as the change in the optical density (OD) resulting from the reaction between thiol groups and DTNB in the dough, the following results were obtained:

| Hexose oxidase GOD units/kg flour | $OD_{412}$ |
|---|---|
| 0 | 0.297 |
| 100 | 0.285 |
| 250 | 0.265 |
| 875 | 0.187 |
| 1250 | 0.138 |

Thus, this experiment showed a significant decrease in OD indicating a reduction of the content of free thiol groups which was proportionate to the amount of hexose oxidase activity added.

2.4. Improvement of the Rheological Characteristics of Dough by the Addition of Hexose Oxidase The above dough was subjected to extensigraph measurements according to AACC Method 54-10 with and without the addition of an amount of the hexose oxidase preparation corresponding to 100 units/kg flour of hexose oxidase activity. The dough without addition of enzyme served as a control.

The principle of the above method is that the dough after forming is subjected to a load-extension test after resting, at 30° C. for 45, 90, 135 and 180 minutes, respectively, using an extensigraph capable of recording a load-extension curve (extensigram) which is an indication of the doughs resistance to physical deformation when stretched. From this curve, the resistance to extension, B (height of curve) and the extensibility, C (total length of curve) can be calculated. The B/C ratio (D) is an indication of the baking strength of the flour dough.

The results of the experiment is summarized in Table 2.1 below.

TABLE 2.1

Extensigraph measurements of dough supplemented with 100 GOD units/kg flour of hexose oxidase (HOX).

| Sample | Time, min | B | C | D = B/C |
|---|---|---|---|---|
| Control | 45 | 230 | 180 | 1.3 |
| HOX | 45 | 320 | 180 | 1.8 |
| Control | 90 | 290 | 161 | 1.8 |
| HOX | 90 | 450 | 148 | 3.0 |
| Control | 135 | 290 | 167 | 1.7 |
| HOX | 135 | 490 | 146 | 3.4 |
| Control | 180 | 300 | 168 | 1.8 |
| HOX | 180 | 500 | 154 | 3.2 |

It is apparent from this table that the addition of hexose oxidase (HOX) has an improving effect on the doughs resistance to extension as indicated by the increase in B-values. This is reflected in almost a doubling of the B/C ratio as a clear indication that the baking strength of the flour is significantly enhanced by the hexose oxidase addition.

In a similar experiment, 100 units/kg flour of a commercial glucose oxidase product was added and the above parameters measured in the same manner using a dough without enzyme addition as a control. The results of this experiment is shown in Table 2.2 below:

TABLE 2.2

Extensigraph measurements of dough supplemented with
100 GOD units/kg flour of glucose oxidase (GOX).

| Sample | Time, min | B | C | D = B/C |
|---|---|---|---|---|
| Control | 45 | 240 | 180 | 1.3 |
| GOX | 45 | 290 | 170 | 1.7 |
| Control | 90 | 260 | 175 | 1.5 |
| GOX | 90 | 360 | 156 | 2.3 |
| Control | 135 | 270 | 171 | 1.6 |
| GOX | 135 | 420 | 141 | 3.0 |

When the results for the above two experiments are compared with regard to differences between control dough and the hexose oxidase or glucose oxidase supplemented doughs it appeared that hexose oxidase has a stronger strengthening effect than glucose oxidase. Furthermore, the B/C ratio increased more rapidly with hexose oxidase relative to glucose oxidase which is a clear indication that enhancement of the baking strength is being conferred more efficiently by hexose oxidase than by glucose oxidase.

Example 3

Dough Improving Effect of Hexose Oxidase Extracted from *Chondrus crispus*

For this experiment fresh *Chondrus crispus* seaweed fronds were harvested along the coast of Hirsholmene, Denmark. Hexose oxidase was isolated using two different extraction procedures, and the materials from both were pooled for the below dough improving experiment.

3.1. Purification of Hexose Oxidase from *Chondrus crispus* I 954 g of the fresh fronds was rinsed in distilled water, dried with a towel and scored in liquid nitrogen. The seaweed was blended using a Waring blender and 1908 ml of 0.1 M sodium phosphate buffer, 1 M NaCl, pH 6.8 was added to the blended seaweed. The mixture was extracted under constant stirring for 4 days at 5° C., followed by centrifugation of the mixture at 20,000×g for 30 minutes.

The resulting 1910 ml supernatant (351.1 U/ml) was concentrated to 440 ml at 40° C. in a Büchi Rotavapor R110. The concentrate was ammonium sulphate fractionated to 250. The mixture was stirred for 30 minutes and centrifuged for 20 minutes at 47,000×g. The supernatant (395 ml) was dialysed overnight against 20 l of 10 mM triethanolamine (TEA) buffer, pH 7.3 to a final volume of 610 ml (367.1 U/ml).

The above 610 ml was applied in two runs to a 2.6×25 cm column with 130 ml Q-Sepharose FF equilibrated in 20 mM TEA buffer, pH 7.3. The column was washed with the equilibration buffer and the bound proteins were eluted using 800 ml gradient from 0 to 0.8 M NaCl in equilibration buffer. The column was eluted at 4 ml/minute and fractions of 12 ml collected. Fractions containing the hexose oxidase activity were collected and pooled to a final volume of 545 ml (241.4 U/ml).

3.2. Purification of Hexose-Oxidase from *Chondrus crispus* II 1250 g of the fresh fronds was rinsed in distilled water, dried with a towel and stored in liquid nitrogen. The seaweed was blended in a Waring blender followed by the addition of 2500 ml 0.1 M sodium phosphate buffer, 1 M NaCl pH 6.8. The mixture was extracted under continuous stirring for 4 days at 5° C. followed by centrifugation at 20,000×g for 30 minutes. The resulting 2200 ml supernatant (332.6 U/ml) was concentrated to 445 ml at 40° C. using a Büchi Rotavaper R110. The resulting concentrate was ammonium sulphate fractionated to 25%. The mixture was stirred for 30 minutes and centrifuged for 20 minutes' at 47,000×g. The precipitate was discarded. The 380 ml supernatant was dialysed overnight against 20 l 10 mM TEA buffer, pH 7.3, to a final volume of 850 ml (319.2 U/ml).

The above 850 ml was applied to a 2.5×25 cm column with 130 ml Q-Sepharose FF equilibrated in 20 mM TEA buffer, pH 7.3. The column was washed with the equilibration buffer and the bound proteins were eluted using 800 ml gradient from 0 to 0.8 M NaCl in equilibration buffer. The column was eluted at 4 ml/minute and fractions of 12 ml collected. Fractions containing the hexose oxidase activity were collected and pooled to a final volume of 288 ml.

The retentate from the above step was applied to a 2.6×31 cm column with 185 ml metal chelating sepharose FF loaded with $Ni^{2+}$ and equilibrated in 50 mM sodium phosphate, 1 M NaCl, pH 7.4. The bound proteins were eluted with a 740 ml gradient of 0 to 35 mM imidazole, pH 4.7 in equilibration buffer. The column was eluted at 2 ml/minute and fractions of 11 ml was collected. Fractions 41-54 (140 ml, 352.3 U/ml) were pooled. Some hexose oxidase did run through the column.

3.3. Pooling and Concentrating of Extracts

The run through and the 140 ml from purification II and the 545 ml from purification I were pooled to a final volume of 1120 ml (303.6 U/ml). The 1120 ml was rotation evaporated into a volume of 210 ml followed by dialysis overnight against 20 l of 10 mM TEA buffer, pH 7.3, to a final volume of 207 ml (1200.4 U/ml).

3.3.1. Anion Exchange Step

The retentate resulting from the above step was applied to a 2.6×25 cm column with 130 ml Q-sepharose FF equilibrated in 20 mM triethanolamine, pH 7.3. The column was washed with the equilibration buffer and the bound proteins eluted using 800 ml gradient from 0 to 0.8 M NaCl in equilibration buffer. The column was eluted at 4 ml/minute and fractions of 12 ml collected. Fractions 30-50 containing the hexose oxidase activity (260 ml, 764.1 U/ml) were collected and pooled.

3.3.2. Other Enzyme Activity

The above pooled solution was tested for the following enzymatic side activities catalase, protease, xylanase, α- and β-amylase and lipase. None of these activities were found in the solution.

3.4. Improvement of the Rheological Characteristics of Dough by the Addition of Hexose Oxidase A dough was prepared from wheat flour, water and salt and 0, 72, 216 and 360 units per kg of flour, respectively of the above hexose oxidase preparation was added hereto. The dough without addition of enzyme served as a control. In addition two doughs were prepared to which was added 216 and 360 units per kg of flour respectively, of Gluzyme, a glucose oxidase available from Novo Nordisk A/S, Denmark.

The doughs were subjected to extensigraph measurements according to a modification of the above AACC Method 54-10. The results of the experiment are summarized in Table 3.1 below.

TABLE 3.1

Extensigraph measurements of dough supplemented with hexose oxidase (HOX) or glucose oxidase (units per kg flour)

| Sample | Time, min. | B | C | D = B/C |
|---|---|---|---|---|
| Control | 45 | 250 | 158 | 1.6 |
| HOX 72 U/kg | 45 | 330 | 156 | 2.1 |

TABLE 3.1-continued

Extensigraph measurements of dough supplemented with hexose oxidase (HOX) or glucose oxidase (units per kg flour)

| Sample | Time, min. | B | C | D = B/C |
|---|---|---|---|---|
| HOX 216 U/kg | 45 | 460 | 153 | 3.0 |
| HOX 360 U/kg | 45 | 580 | 130 | 4.5 |
| Gluzyme 72 U/kg | 45 | 350 | 159 | 2.2 |
| Gluzyme 216 U/kg | 45 | 340 | 148 | 2.3 |
| Gluzyme 360 U/kg | 45 | 480 | 157 | 3.1 |
| Control | 90 | 290 | 164 | 1.8 |
| HOX 72 U/kg | 90 | 470 | 145 | 3.2 |
| HOX 216 U/kg | 90 | 650 | 142 | 4.6 |
| HOX 360 U/kg | 90 | 870 | 116 | 7.5 |
| Gluzyme 72 U/kg | 90 | 450 | 147 | 3.1 |
| Gluzyme 216 U/kg | 90 | 480 | 138 | 3.5 |
| Gluzyme 360 U/kg | 90 | 500 | 152 | 3.2 |
| Control | 135 | 330 | 156 | 2.1 |
| HOX 72 U/kg | 135 | 540 | 129 | 4.2 |
| HOX 216 U/kg | 135 | 750 | 125 | 6.0 |
| HOX 360 U/kg | 135 | 880 | 117 | 7.5 |
| Gluzyme 72 U/kg | 135 | 510 | 136 | 3.8 |
| Gluzyme 216 U/kg | 135 | 550 | 122 | 4.5 |
| Gluzyme 360 U/kg | 135 | 560 | 121 | 4.6 |

It is evident from the above table that the addition of hexose oxidase (HOX) or glucose oxidase had an improving effect on the resistance of doughs to extension as indicated by the increase in B-values. This is reflected in an increase of the B/C ratio as a clear indication that the baking strength of the flour was enhanced significantly by the addition of enzymes.

It is also evident that the hexose oxidase had a higher strengthening effect than glucose oxidase. Furthermore, the B/C ratio increased more rapidly with hexose oxidase relative to glucose oxidase which is a clear indication that enhancement of the baking strength is being conferred more efficiently by hexose oxidase than by glucose oxidase.

Example 4

Dough Improving Effect of Hexose Oxidase Extracted from *Chondrus crispus*

4.1. Purification of Hexose Oxidase from *Chondrus crispus*

Fresh *Chondrus crispus* fronds were harvested along the coast of Brittany, France. 2285 g of this fresh material was rinsed in distilled water, dried with a towel and stored in liquid nitrogen. The seaweed was blended in a Waring blender followed by addition of 4570 ml 0.1 M sodium phosphate buffer, 1 M NaCl pH 6.8. The mixture was extracted under continuous magnetic stirring for 4 days at 5° C. followed by centrifugation at 20,000×g⁻ for 30 minutes.

The resulting 4930 ml supernatant (624.4 U/ml) was concentrated to 1508 ml at 40° C. using a Büchi Rotavapor R110. The obtained concentrate was polyethylenglycol fractionated to 3's (w/v). The mixture was stirred for 30 minutes and centrifuged for 30 minutes at 47,000×g. The pellet was discarded. The 1470 ml suoernatant (2118.7 U/ml) was PEG fractionated to 24%. The mixture was stirred for 30 minutes and centrifuged for 30 minutes at 47,000×g. The supernatant was discarded and the 414.13 g of precipitate was resuspended in 200 ml 20 mm TEA buffer, pH 7.3, followed by dialysis over night at 5° C. against 20 l 10 mM TEA buffer, pH 7.3.

After dialysis the volume was 650 ml (2968.6 U/ml). The suspension was centrifuged for 30 minutes at 20,000×g. The precipitate was discarded and the supernatant was diluted to 3200 ml with distilled water.

The above 3200 ml (829.9 U/ml) was applied to a 10×14 cm column with 1100 ml Q-Sepharose FF equilibrated in 20 mM TEA buffer, pH 7.3. The column was washed with the equilibration buffer and the bound proteins were eluted using 15,000 ml gradient from 0 to 0.8 M NaCl in equilibration buffer. The column was eluted at 50 ml/minute. Hexose oxidase did run through the column and 840 ml of this was collected.

The 840 ml suspension was treated with kieselguhr and concentrated to 335 ml (2693.3 U/ml).

The above 335 ml was applied to a 3 l Sephadex G25C desalting column 10×40 cm. The column was equilibrated in 20 mM TEA buffer, pH 7.3, eluted at a flow rate of 100 ml/minute and 970 ml eluate was collected. This eluate was applied to a 10×14 cm column with 1100 ml Q-Sepharose FF equilibrated in 20 mM TEA, pH 7.3. The column was washed with the equilibration buffer and bound proteins eluted using a 15,000 ml gradient of 0 to 0.8 M NaCl in equilibration buffer. The column was eluted at 50 ml/min. Hexose oxidase did run through the column and 1035 ml of this was collected.

To the above eluate (1035 ml) ammonium sulphate was added to a final concentration of 2 M. The mixture was then applied in two runs to a 5×10 cm column with 200 ml phenyl sepharose HP equilibrated in 25 mM sodium phosphate buffer, pH 6.3 and 2 M $(NH_4)_2SO_4$. The column was washed with equilibration buffer followed by eluting the bound proteins at a flow rate of 50 ml/minute using 5,000 ml gradient from 2 M to 0 M $(NH_4)_2SO_4$ in 25 mM sodium phosphate buffer. Fractions of 500 and 29 ml, respectively were collected from run 1 and 2. Fraction 5 in run 1 and fractions 27-42 in run 2 containing the hexose oxidase activity were pooled to a total of 1050 ml (563.9 U/ml).

The above pool was desalted by a 3 l Sephadex G25C gel filtration column. The column was equilibrated in 20 mM TEA buffer, oH 7.3, eluted at a flow rate of 100 ml/minute and 1,000 ml eluate was collected.

The 1,000 ml eluate was concentrated to 202, ml (2310.2 U/ml) and this preparation was used for following rheology testing.

4.2. Improvement of the Rheological Characteristics of Dough by the Addition of Hexose Oxidase A dough was prepared from wheat flour, water and salt and 0, 288, 504 and 720 oxidoreductase units per kg of flour, respectively of the above hexose oxidase preparation was added hereto. The dough without addition of enzyme served as a control. In addition two doughs were prepared to which was added 288 and 504 oxidoreductase units per kg of flour respectively, of Gluzyme, a glucose oxidase available from Novo Nordisk A/S, Denmark.

The doughs were subjected to extensigraph measurements according to a modification of AACC Method 54-10.

The results of the experiment are summarized in Table 4.1 below.

TABLE 4.1

Extensigraph measurements of dough supplemented with hexose oxidase (HOX) or glucose oxidase (Units per kg flour).

| Sample | Time, min. | B | C | D = B/C |
|---|---|---|---|---|
| Control | 45 | 210 | 171 | 1.2 |
| HOX 288 U/kg | 45 | 490 | 139 | 3.5 |
| HOX 504 U/kg | 45 | 640 | 122 | 5.2 |
| HOX 720 U/kg | 45 | 730 | 109 | 6.7 |
| Gluzyme 288 U/kg | 45 | 350 | 165 | 2.1 |
| Gluzyme 504 U/kg | 45 | 385 | 153 | 2.5 |
| Gluzyme 720 U/kg | 45 | 435 | 148 | 2.9 |

TABLE 4.1-continued

Extensigraph measurements of dough supplemented with hexose oxidase (HOX) or glucose oxidase (Units per kg flour).

| Sample | Time, min. | B | C | D = B/C |
|---|---|---|---|---|
| Control | 90 | 275 | 182 | 1.5 |
| HOX 288 U/kg | 90 | 710 | 130 | 5.5 |
| HOX 504 U/kg | 90 | 825 | 106 | 7.8 |
| HOX 720 U/kg | 90 | 905 | 107 | 8.5 |
| Gluzyme 288 U/kg | 90 | 465 | 153 | 3.0 |
| Gluzyme 504 U/kg | 90 | 515 | 135 | 3.8 |
| Gluzyme 720 U/kg | 90 | 540 | 140 | 3.9 |
| Control | 135 | 280 | 175 | 1.6 |
| HOX 288 U/kg | 135 | 745 | 102 | 7.3 |
| HOX 504 U/kg | 135 | 920 | 94 | 9.8 |
| HOX 720 U/kg | 135 | — | 80 | — |
| Gluzyme 288 U/kg | 135 | 525 | 129 | 4.1 |
| Gluzyme 504 U/kg | 135 | 595 | 129 | 4.6 |
| Gluzyme 720 U/kg | 135 | 630 | 121 | 5.2 |

It is apparent from the above results that the addition of hexose oxidase (HOX) or glucose oxidase has an improving effect on the resistance of doughs to extension as indicated by the increase in B-values. This is an increase of the B/C ratio.

It is also apparent that hexose oxidase has a stronger strengthening effect than that of glucose oxidase, the strengthening effect of both enzymes being proportional to the amount of enzyme added. Furthermore, the B/C ratio increased more rapidly with hexose oxidase relative to glucose oxidase which is a clear indication that enhancement of the baking strength is being conferred more efficiently by hexose oxidase than by glucose oxidase.

Example 5

Improving Effect of Hexpse Oxidase Extracted from *Chondrus crispus* on the Specific Volume of Bread 5.1. Purification of Hexose Oxidase from *Chondrus crispus*

Fresh *Chondrus crispus* fronds were harvested along the coast of Brittany, France. 2191 g of this fresh material was rinsed in distilled water, dried with a towel and stored in liquid nitrogen. The seaweed was blended in a Waring blender followed by addition of 4382 ml 0.1 M sodium phosphate buffer, 1 M NaCl and pH 6.8. The mixture was extracted under continuously magnetic stirring for 4 days at 5° C. followed by centrifugation at 20,000×g for 20 minutes.

The resulting 4600 ml supernatant (745.1 U/ml) was concentrated to 850 ml at 40° C. in a Büchi Rotavapor R110. This concentrate (3525.9 U/ml) was polyethylene glycol fractionated to 3% (w/v). The mixture was stirred for 30 minutes and centrifuged for 30 minutes at 20,000×g. The precipitate was discarded. The 705 ml supernatant (2439.8 U/ml) was PEG fractionated to 25%. The mixture was stirred for 30 minutes and centrifuged for 30 minutes at 20,000×g. The supernatant was discarded and the 341 g of precipitate was resuspended in 225 ml 20 mM TEA buffer, pH 7.3. The suspension (500 ml) was desalted on a 3 l Sephadex G25C desalting column 10×40 cm. The column was equilibrated in 20 mM TEA buffer, pH 7.3, and eluted at a flow rate of 100 ml/minute. 1605 ml eluate was collected.

To the above eluate (687.5 U/ml) ammonium sulphate was added to a final concentration of 2 M. The mixture was then applied in two runs to a 5×10 cm column with 200 ml phenyl sepharose HP equilibrated in 25 mM sodium phosphate buffer, pH 6.3 and 2 M $(NH_4)_2SO_4$. The column was washed with equilibration buffer followed by elution of the bound proteins at a flow rate of 50 ml/minute using 5,000 ml gradient from 2 M to 0 M $(NH_4)_2SO_4$ in 25 mM sodium phosphate buffer. Fractions of 29 ml was collected. Fractions 85-105 in run 1 and fractions 36-69 in run 2 containing the hexose activity were pooled to a total of 1485 ml (194.7 U/ml).

The above pool was desalted by a 3 l Sephadex G25C gelfiltration column, the same as used in 4.1. The column was equilibrated in 20 mM TEA buffer, pH 7.3, and eluted at a flow rate of 100 ml/minute. 1,200 ml eluate was collected.

The 1,200 ml eluate was concentrated to 685 ml (726.2 U/ml) and used for baking experiments.

5.2. Improvement of the Specific Volume of Bread by Adding Hexose Oxidase to the Dough A dough was prepared from 1500 g of flour, 90 g of yeast, 24 g of salt, 24 g of sugar and 400 BU of water and 0 or 108 units of the above purified hexose oxidase and 108 units of Gluzyme (glucose oxidase available from Novo Nordisk, Denmark) per kg flour, respectively was added hereto. The dough was mixed on a Hobart mixer for 2-9 minutes at 25° C. and divided into two parts followed by resting for 10 minutes at 30° C. in a heating cabinet, moulding with a Formula 3/17/7 and proofing for 45 minutes at 34° C. and 85% RH. The thus proofed dough was baked at 220° C. for 17 minutes with 12 sec. steam in a Bago oven.

The results of the experiment are summarized in table 5.1 below.

TABLE 5.1

Improvement of specific volumes of bread prepared from dough supplemented with hexose oxidase or glucose oxidase (Units per kg flour)

| | Total volume | Total weight | Specific volume |
|---|---|---|---|
| Control | 5325 | 1027 | 5.18 |
| Hexose oxidase 108 U/kg | 6650 | 1036 | 6.41 |
| Gluzyme 108 U/kg | 6075 | 1030 | 5.89 |

It is evident from the above table that the addition of hexose oxidase or glucose oxidase had an increasing effect on the total volume, the weight being essentially the same. This is reflected in an increase of the specific volume as compared to the bread baked without addition of enzymes.

It is also evident that hexose oxidase has a significantly larger effect on the increase of the specific volume than had glucose oxidase at the same dosage.

Example 6

Characterization of the Purified Hexose Oxidase

Preparations from the above purifications were used for characterization of hexose oxidase.

6.1 Staining for Hexose Activity after Non-Denaturing PAGE

Hexose oxidase activity was analyzed by native PAGE using precast 8-16% Tris-glycine Novex gels according to the manufactures instructions (Novex, San Diego, USA). After electrophoresis the gels were stained for hexose oxidase activity by incubation of the gel in a solution containing 50 mM sodium phosphate buffer, pH 6.0, 100 mM glucose, 50 mg/l phenazine methosulphate (Sigma P9625) and 250 mg/l nitroblue tetrazolium (Sigma as N6876) as described in the PhD thesis by Witteveen, C. F. B. (1993) "Gluconate formation and polyol metabolism in *Aspergillus niger*". After about 30 minutes the hexose oxidase activity was visible as a double band very close to each other. The same double band was also seen when a native PAGE of hexose oxidase was silver stained. The molecular weight of purified hexose oxidase was determined to 144 kD by native PAGE. Half the gel was silver strained, the other half was activity stained. As standards were used bovine serum albumin (67 kD), lactate dehydrogenase (140 kD), catalase (232 kD), ferritin (440 kD) and thyroglo-ubulin (669 kD).

The molecular weight was also determined on material which was first applied to a native PAGE as described above, after activity staining the hexose oxidase band was, excised from the gel and then electroeluted using an Electro-Eluter (model 422, Bio-Rad, CA, USA) according to the manufacturer's recommendations. The electroeluted protein was subjected to SDS-PAGE and silver strained. This material gave "one" double band at about 70 kDa in SDS-PAGE gels. The electroeluted hexose oxidase is therefore a dimer of two subunits.

6.3 Determination of pI of Hexose Oxidase

Samples containing hexose oxidase activity were analyzed by isoelectric focusing (IEF) using a precast 3-10 IEF gel according to the manufacturer's recommendations (Novex, San Diego, US). After electrophoresis half of the gel was silver stained and the other hale nitroblue tetrazolium stained as described in 6.1.

Hexose oxidase stained as a double band. The pI of the first band was 4.79, pI of the second band was 4.64. As standards were used trypsinogen (9.30), lentil lectin basic band (8.65), lentil lectin middle band (8.45), lentil lectin acid band (8.15), horse myoglobin acidic band (6.85), human car-boric anhydrase B (5.85), (3-lactoglobulin A (5.20), soy bean trypsin inhibitor (4.55) and amyloglucosidase (3.50).

6.4 Determination of $K_m$ of Hexose Oxidase for Different Sugars $K_m$ of hexose oxidase was determined for 7 different sugars as described in 1.2.3. Results are summarized in table 6.1 below.

TABLE 6.1

Determination of $K_m$ of hexose oxidase for different sugars

| Substrate | $K_m$ (mM) | CV (mM) |
|---|---|---|
| D-glucose | 2.7 | 0.7 |
| D-galactose | 3.6 | 1 |
| cellobiose | 20.2 | 7.8 |
| maltose | 43.7 | 5.6 |
| lactose | 90.3 | 20.6 |
| xylose | 102 | 26 |
| arabinose | 531 | 158 |

(CV = coefficient of variation)

6.5 Determination of a Peptide Sequence of the Hexose Oxidase

50 µl from the electroeluted mixture in 6.2 was suspended in 450 µl 0.10 triflouracetic acid (TFA).

To remove the Tris, glycine and SDS, the above mixture was subjected to chromatography on reverse-phase HPLC. The resulting solution was applied in 9 runs to a 4.6×30 cm Brownlee C2 column equilibrated in 0.1% TFA. The column was washed in equilibration buffer and bound peptides eluted with a 14 ml gradient from 10 to 80% acetonitrile in 0.1% TFA, at a flow rate of 0.7 ml/min. Fractions from the largest peak containing the enzyme were collected and freeze dried.

6.5.1 Endproteinase Lys-C digestion

The resulting freeze dried enzyme was dissolved in 50 µl 8M urea, 0.4 M $NH_4HCO_3$, pH 8.4. Denaturation and reduction of the protein was carried out by the addition of 5 µl 45 mM di-thiothreitol and under an overlay of $N_2$ at 50° C. for 15 min. The solution was cooled to room temperature and 5 µl 100 mM iodoacetamide was added, the cysteines being derivatized for 15 min. at room temperature in the dark under $N_2$. Subsequently, the solution was suspended in 135 µl water and digestion was carried out at 37° C. under N2 for 24 hours by addition of 5 µg endoproteinase Lys-C dissolved in 5 µl water. The reaction was terminated by freezing the reaction mixture at −20° C.

6.5.2 Reverse-Phase HPLC Separation of Peptides

The resulting peptides were separated by reverse-phase HPLC on a VYDAC C18 column 0.46×15 cm (The Separation Group, CA, USA) using as solvent A 0.1% TFA in water and as solvent 0.1 TFA in acetonitrile.

6.5.3 Peptide sequencing

Sequencing was performed on an Applied Biosystems 476A sequencer (Applied Biosystems, CA, USA) using pulsed-liquid fast cycles according to the manufacturer's instructions. A peptide having the below amino acid sequence was identified:

(SEQ ID NO.: 1)
D P G Y I V I D V N A G T P D K P D P.

The invention claimed is:

1. A dough improving composition comprising an oxidoreductase, which is at least capable of oxidizing maltose, flour and at least one further dough ingredient or dough additive, wherein said oxidoreductase is hexose oxidase.

2. A composition according to claim 1, wherein the oxidoreductase is derived from a source selected from an algal species, a plant species and a microbial species.

3. A composition according to claim 1, wherein the hexose oxidase is derived from *Chondrus crispus*.

4. A composition according to claim 1, which is a premixture useful for preparing a baked product or in making a noodle product or an alimentary paste product.

5. A composition according to claim 1, which comprises an additive selected from the group consisting of an emulsifying agent and a hydrocolloid.

6. A composition according to claim 5, wherein the hydrocolloid is selected from the group consisting of an alginate, a carrageenan, a pectin and a vegetable gum.

7. A dough comprising a dough improving composition comprising an oxidoreductase which is at least capable of oxidizing maltose and at least one further dough ingredient or dough additive, and flour, wherein said oxido reductase is hexose oxidase.

8. A flour dough comprising an oxidoreductase which is at least capable of oxidizing maltose and flour, wherein said oxido reductase is hexose oxidase.

9. The flour dough according to claim 8, wherein said flour is selected from the group consisting of wheat flour, rice flour, maize flour, barley flour, rye flour, durra flour and mixtures thereof.

10. The flour dough according to claim 8, wherein said flour dough comprises at least one further enzyme.

11. The flour dough according to claim 8, wherein said flour dough comprises at least one further enzyme and wherein said further enzyme is selected from the group consisting of cellulase, a hemicellulase, a xylanase, a starch degrading enzyme, a glucose oxidase, a lipase and a protease.

12. The flour dough according to claim 8, wherein said hexose oxidase is derived from a source selected from the group consisting of an algal species, a plant species and a microbial species.

13. The flour dough according to claim 8, wherein said hexose oxidase is derived from *Chondrus crispus*.

14. A baked or dried product produced from a flour dough wherein said flour dough comprises an oxidoreductase which is at least capable of oxidizing maltose, wherein said oxidoreductase is hexose oxidase.

15. The baked or dried product according to claim 14, wherein said flour is selected from the group consisting of wheat flour, rice flour, maize flour, barley flour, rye flour, durra flour and mixtures thereof.

16. The baked or dried product according to claim 14, wherein said flour dough comprises at least one further enzyme.

17. The baked or dried product according to claim 14, wherein said flour dough comprises at least one further enzyme and wherein said further enzyme is selected from the group consisting of cellulase, a hemicellulase, a xylanase, a starch degrading enzyme, a glucose oxidase, a lipase and a protease.

18. The baked or dried product according to claim 14, wherein said hexose oxidase is derived from a source selected from the group consisting of an algal species, a plant species and a microbial species.

19. The baked or dried product according to claim 14, wherein said hexose oxidase is derived from *Chondrus crispus*.

20. The baked product according to claim 14, wherein said baked product is bread.

21. The dried product according to claim 14, wherein said dried product is a noodle or an alimentary paste product.

* * * * *